(12) United States Patent
Toro et al.

(10) Patent No.: US 7,462,755 B2
(45) Date of Patent: Dec. 9, 2008

(54) ABSORBENT ARTICLE COMPRISING EDGE BARRIERS COMPRISING A LIQUID ABSORBENT THERMOPLASTIC COMPOSITION

(75) Inventors: Carlo Toro, Cepagatti (IT); Enzo Pompei, Pescara (IT); Giovanni Carlucci, Chieti (IT); Marco Digiacomantonio, Pescara (IT); Fiorello Salone, Pescara (IT)

(73) Assignee: The Procter & Gamble Company, Cincinnati, OH (US)

( * ) Notice: Subject to any disclaimer, the term of this patent is extended or adjusted under 35 U.S.C. 154(b) by 300 days.

(21) Appl. No.: 11/087,475

(22) Filed: Mar. 23, 2005

(65) Prior Publication Data

US 2005/0215967 A1  Sep. 29, 2005

(51) Int. Cl.
*A61F 13/15* (2006.01)
(52) U.S. Cl. .................... 604/378; 604/379; 604/367; 604/368; 604/385.101; 604/374
(58) Field of Classification Search ............... 604/378, 604/379, 367, 368, 385.101, 374
See application file for complete search history.

(56) References Cited

U.S. PATENT DOCUMENTS

| | | | |
|---|---|---|---|
| 3,156,242 A | 11/1964 | Crowe | |
| 3,929,135 A | 12/1975 | Thompson | |
| 3,989,867 A | 11/1976 | Sisson | |
| 4,200,103 A | 4/1980 | Black et al. | |
| 4,310,593 A | 1/1982 | Gross | |
| 4,324,246 A | 4/1982 | Mullane | |
| 4,342,314 A | 8/1982 | Radel | |
| 4,402,604 A | 9/1983 | Nash | |
| 4,411,760 A | 10/1983 | Guerriero et al. | |
| 4,415,185 A | 11/1983 | Vinciguerra et al. | |
| 4,463,045 A | 7/1984 | Ahr | |
| 4,591,523 A | 5/1986 | Thompson | |
| 4,609,518 A | 9/1986 | Curro | |
| 4,629,643 A | 12/1986 | Curro | |
| 4,637,819 A | 1/1987 | Ouellette | |
| 4,654,039 A | 3/1987 | Brandt | |
| 4,695,236 A | 9/1987 | Predohl et al. | |
| 4,695,422 A | 9/1987 | Curro et al. | |
| 4,718,898 A | 1/1988 | Decowski, Jr. et al. | |
| RE32,649 E | 4/1988 | Brandt | |
| 4,839,216 A | 6/1989 | Curro et al. | |

(Continued)

FOREIGN PATENT DOCUMENTS

DE      100 26 861 A      12/2001

(Continued)

OTHER PUBLICATIONS

PCT International Search Report dated Jun. 14, 2005.

*Primary Examiner*—Jacqueline F. Stephens
(74) *Attorney, Agent, or Firm*—Gary J. Foose; Roddy M. Bullock (57) ABSTRACT

The present invention relates to absorbent articles, typically for feminine protection, comprising a topsheet, a backsheet, an absorbent element positioned between the topsheet and the backsheet, and at least a fluid acquisition/distribution layer. The absorbent article also comprises edge barrier elements for intercepting fluids. The edge barrier elements comprise a liquid absorbent thermoplastic composition comprising a polymeric base material having particles of water-insoluble water-swellable absorbent material dispersed therein, and are comprised between the absorbent core and the at least one fluid acquisition/distribution layer.

7 Claims, 3 Drawing Sheets

U.S. PATENT DOCUMENTS

| | | | |
|---|---|---|---|
| 4,929,722 A | 5/1990 | Partain, III et al. | |
| 4,946,870 A | 8/1990 | Partain, III. et al. | |
| 4,950,254 A | 8/1990 | Andersen | |
| 4,952,618 A | 8/1990 | Olsen | |
| 4,977,211 A | 12/1990 | Doi | |
| 4,988,344 A * | 1/1991 | Reising et al. | 604/368 |
| 4,995,333 A | 2/1991 | Keller et al. | |
| 5,006,394 A | 4/1991 | Baird | |
| 5,009,653 A | 4/1991 | Osborn, III | |
| 5,026,800 A | 6/1991 | Kimura et al. | |
| 5,074,856 A | 12/1991 | Coe et al. | |
| 5,175,046 A | 12/1992 | Nguyen | |
| 5,275,591 A | 1/1994 | Mavinkurve | |
| 5,300,494 A | 4/1994 | Brode, II et al. | |
| 5,378,472 A | 1/1995 | Muzzarelli | |
| 5,415,640 A | 5/1995 | Kirby et al. | |
| 5,433,715 A | 7/1995 | Tanzer | |
| 5,490,847 A | 2/1996 | Correa et al. | |
| 5,533,991 A | 7/1996 | Kirby et al. | |
| 5,562,932 A | 10/1996 | Rieker | |
| 5,567,744 A | 10/1996 | Nagata | |
| 5,591,510 A | 1/1997 | Junker | |
| 5,597,811 A | 1/1997 | Gruber | |
| 5,621,088 A | 4/1997 | Gruber | |
| D394,503 S | 5/1998 | Perrini | |
| 5,755,710 A | 5/1998 | Menard | |
| 5,810,800 A | 9/1998 | Hunter et al. | |
| 5,855,719 A | 1/1999 | Menard | |
| 5,895,379 A | 4/1999 | Litchholt et al. | |
| 5,961,505 A | 10/1999 | Coe et al. | |
| 6,015,608 A | 1/2000 | Koslow | |
| 6,140,550 A | 10/2000 | Beihoffer et al. | |
| 6,403,857 B1 | 6/2002 | Leptick et al. | |
| 6,458,877 B1 | 10/2002 | Ahmed et al. | |
| 6,465,379 B1 | 10/2002 | Cook et al. | |
| 6,495,612 B1 | 12/2002 | Corzani et al. | |
| 6,498,201 B1 | 12/2002 | Corzani et al. | |
| 6,534,572 B1 | 3/2003 | Ahmed et al. | |
| 6,562,742 B2 | 5/2003 | Dutkiewicz et al. | |
| 6,677,394 B1 | 1/2004 | Butterbach et al. | |
| 6,822,135 B2 | 11/2004 | Soerens et al. | |
| 7,037,298 B2 | 5/2006 | Ohshima et al. | |
| 2001/0014797 A1 | 8/2001 | Nakaoka et al. | |
| 2002/0039869 A1 | 4/2002 | Achille | |
| 2003/0012928 A1 | 1/2003 | Malowaniec et al. | |
| 2003/0040729 A1 | 2/2003 | Malowaniec et al. | |
| 2003/0065299 A1 | 4/2003 | Carlucci et al. | |
| 2003/0093051 A1 | 5/2003 | Malowaniec et al. | |
| 2003/0109628 A1 | 6/2003 | Bonfanti et al. | |
| 2003/0113548 A1 | 6/2003 | Corzani et al. | |
| 2003/0120233 A1 | 6/2003 | Ohshima et al. | |
| 2003/0171464 A1 | 9/2003 | Corzani et al. | |
| 2004/0058159 A1 | 3/2004 | Gagliardi et al. | |
| 2004/0059018 A1 | 3/2004 | Gagliardi et al. | |
| 2004/0065232 A1 | 4/2004 | Lykke | |
| 2004/0127883 A1 | 7/2004 | Petryk et al. | |
| 2005/0273067 A1 | 12/2005 | Malowaniec et al. | |

FOREIGN PATENT DOCUMENTS

| | | |
|---|---|---|
| DE | 10 2004 055 049 A1 | 5/2006 |
| EP | 0 130 848 A2 | 1/1985 |
| EP | 0 134 086 A1 | 3/1985 |
| EP | 0 612 233 B1 | 4/1996 |
| EP | 0 349 241 B1 | 8/1996 |
| EP | 1 013 291 A1 | 6/2000 |
| EP | 1 013 291 B1 | 6/2005 |
| GB | 2 019 727 A | 11/1979 |
| WO | WO 96/09023 A1 | 3/1996 |
| WO | WO 96/16624 A2 | 6/1996 |
| WO | WO 97/03818 A1 | 2/1997 |
| WO | WO 97/24097 A1 | 7/1997 |
| WO | WO 98/07618 A1 | 2/1998 |

* cited by examiner

ABSORBENT ARTICLE COMPRISING EDGE BARRIERS COMPRISING A LIQUID ABSORBENT THERMOPLASTIC COMPOSITION

FIELD OF THE INVENTION

The present invention relates to absorbent articles, in particular articles for feminine protection like sanitary napkins and panty liners, but also diapers, articles for adult incontinence and the like, which comprise a topsheet, a backsheet, an absorbent core and at least first and second edge barrier elements positioned along opposing edge margins of the absorbent core. The edge barrier elements comprise a liquid absorbent thermoplastic composition comprising a thermoplastic polymeric base material having particles of water-insoluble water swellable absorbent material dispersed therein.

BACKGROUND OF THE INVENTION

Although absorbent articles, such as sanitary napkins or panty liners, have improved a lot the last years with respect to various features like protection and comfort in use, there is still a consumer need for further improvements in these two directions.

Indeed, there exists a real consumer need for absorbent articles, typically for feminine protection articles, having improved liquid handling properties, namely enhanced liquid distribution properties and a liquid holding and containing capacity high enough for use without consumer fears of leakage or staining especially after prolonged period of wearing time, yet which are thin and flexible, thereby offering enhanced fit and comfort.

Leakage of body fluids from the absorbent article typically occurs once the article becomes saturated with absorbed fluid. However in practice leakage of body fluids form the article can also often occur before saturation of the article is reached. Leakage causes staining of the support or associated garments and therefore frequent changing of the absorbent article is often necessary to prevent such staining. Leakage before saturation of the article can be typically caused by exuding body fluid contacting and temporarily saturating the top layers of absorbent material at a central area of the absorbent article, which then causes the body fluid to migrate by wicking or flowing across the upper surface of the article from the central area to the side edges thereof, typically the longitudinal side edges, but also the transverse side edges, before it has penetrated and/or fully diffused within the main bulk of the absorbent core. This effect can be also increased by the presence in absorbent articles of well known fluid acquisition/distribution layers in addition to the main absorbent core, which while on one hand improve the distribution of the absorbed body fluid across a greater surface area of the absorbent core, by also increasing its migration speed, can also bring the fluid more rapidly toward the edges of the absorbent article before it is fully absorbed in the absorbent core, hence potentially causing leakage. This can be also the case if a fluid acquisition/distribution layer is comprised in the absorbent article below the absorbent core, e.g. between the absorbent core and the backsheet. Fluid can in fact in certain conditions rapidly penetrate through the entire thickness of the absorbent core and, before being further absorbed and diffused within the core itself, can be received and spread by an underlying fluid acquisition/distribution layer. This may occur for example with modern, very thin absorbent cores typically constituted by a laminated structure of at least two fibrous layers with particles of absorbent gelling material comprised therebetween. Such structures have a great capacity of absorbing and retaining fluid, but owing to the relatively slow absorption mechanism of the absorbent gelling material particles, are typically advantageously associated to one or more fluid acquisition/distribution layers to promote and increase the diffusion of the fluid, and a more efficient subsequent absorption in the core.

Of course leakage can be also promoted by user's movements during wear which cause the absorbent article to be deformed and compressed, and possibly the fluid to be squeezed out of the core. Particularly for sanitary napkins, prevention of leakage, typically side leakage in the lateral direction, but also in the transverse direction, is of primary importance for users.

A known solution to the problem of leakage in absorbent articles such as sanitary napkins is for example described in patent application GB 2019727, disclosing a sanitary napkin provided with a barrier sheet which is wider than the garment facing surface of the absorbent core and which has longitudinal edge portions which cover the longitudinal sides and preferably also the side margins of the body facing surface of the absorbent core. This solution has however the disadvantage of a relatively complicated structure, especially for application to modern thin absorbent articles, also comprising wings. Moreover, the portions of the barrier sheet folded over part of the body facing surface of the absorbent core actually limit the surface area of the core which is available for direct fluid acquisition.

Alternative types of barriers against leakage in absorbent articles are also described in prior art, constituted for example by seal lines or areas made e.g. by embossing, melting or heat sealing, as disclosed in U.S. Pat. No. 5,275,591, or by application of a water impermeable hot melt adhesive in selected locations, as described in U.S. Pat. No. 4,718,898. All these solutions have the common disadvantage that in any case they create areas in the absorbent structure where absorption is actually inhibited.

Still a further approach to the problem of leakage, and more typically of side leakage in absorbent articles is the provision of physical barriers on the body facing surface of the absorbent article, such as raised elements, or alternatively cuffs or walls which are capable of standing upwards from the body facing surface of the absorbent article during wear. This type of self standing cuffs, preferably also provided with elastic elements, are described for example in U.S. Pat. Nos. 5,074,856, 5,490,847, 5,810,800. The drawbacks of physical barriers are in the rather cumbersome construction, also implying complex manufacturing processes, particularly when present in combination with other rather usual features in absorbent articles, such as for example side wings. They could also be improved for what concerns conformability and comfort in use.

EP 1013291 A1 discloses a hot melt adhesive with superabsorbent polymers. The resulting thermoplastic hot melt adhesive material can be used to provide additional absorption capacity to absorbent structures in absorbent articles, as well as to adhesively bond substrates in the absorbent article, i.e. as an absorbent construction adhesive. The thermoplastic absorbent hot melt adhesive material can be also applied in form of longitudinal and/or transverse edge stripes generically over the core or over the topsheet, in order to provide some sort of barrier effect to body fluids. However, the absorbent articles disclosed in EP 1013291 A1 present the disadvantage of a far less than optimal liquid handling capability, particularly they have a poor capacity of effectively diffuse and distribute the fluid, while at the same time preventing leakage.

It is therefore an object of the present invention to provide an absorbent article having an improved fluid handling capacity, i.e. being capable of effectively acquiring, distributing and absorbing fluid, at the same time minimizing the risk of edge leakage, particularly from the longitudinal side edges.

It is a further object of the present invention to provide an absorbent article that combines in a synergistic way the advantageous and unique characteristics of different materials such as traditional fibrous elements and layers and thermoplastic hot melt adhesive materials which are also absorbent by incorporating absorbent gelling materials.

SUMMARY OF THE INVENTION

The present invention provides an absorbent article having a longitudinal axis and a transverse axis, and comprising a topsheet, a backsheet, an absorbent core positioned between the topsheet and the backsheet, and at least a fluid acquisition/distribution layer.

The absorbent article further comprises at least a first and a second edge barrier element for intercepting fluids, which are positioned on opposing sides of the longitudinal axis and/or of the transverse axis.

The at least first and second edge barrier elements comprise a liquid absorbing thermoplastic composition which comprises a polymeric base material having particles of water-insoluble water-swellable absorbent material dispersed therein, and the at least first and second edge barrier elements are positioned at least partially between the absorbent core and the at least one fluid acquisition/distribution layer.

DETAILED DESCRIPTION OF THE INVENTION

The term "absorbent article" is used herein in a very broad sense including any article able to receive and/or absorb and/or contain and/or retain fluids and/or exudates, especially body fluids/body exudates. "Absorbent articles" as referred to herein include, without being limited to, sanitary napkins, panty liners, incontinence pads, interlabial pads, baby diapers, adult incontinence diapers, and human waste management devices. Particularly, the disposable absorbent article is described below by reference to a sanitary napkin or pantiliner.

The term "disposable" is used herein to describe articles that are not intended to be laundered or otherwise restored or reused as an article (i.e., they are intended to be discarded after a single use and, preferably, to be recycled, composted or otherwise disposed of in an environmentally compatible manner).

As used herein, the term 'wearer-facing', or alternatively 'body-facing', surface refers to the surface of the component of the article generally oriented to face the wearer skin and/or mucosal surface during use of the article. As used herein, the term 'garment facing' surface refers to the opposite outer surface of the article, typically the surface directly facing the garment of a wearer, if worn in direct contact with a garment.

As used herein, the term 'body fluids' refers to any fluid produced by human body occurring naturally including for instance perspiration, urine, menstrual fluids, vaginal secretions and the like, or accidentally like for instance in the case of skin cutting or wounds.

In the following, non-limiting embodiments of the present invention, the main elements of the absorbent article are described.

The absorbent article has a longitudinal axis I-I and a lateral axis II-II, which are perpendicular to each other The absorbent article according to the present invention comprises as main elements: the topsheet, facing the user of the article during use and being liquid pervious in order to allow liquids, particularly body fluids, to pass into the article; the backsheet, providing liquid containment such that absorbed liquid does not leak through the article, this backsheet conventionally providing the garment facing surface of the article; the absorbent core comprised between the topsheet and the backsheet and providing the absorbent capacity of the article to acquire and retain liquid which has entered the article through the topsheet; at least a fluid acquisition/distribution layer, typically comprised between the topsheet and the absorbent core, or between the backsheet and the absorbent core, which is intended to effectively and rapidly diffuse the fluid within its structure, typically by capillary action, after it has acquired said fluid; and at least a first and a second edge barrier elements, distinct from said absorbent core, which are comprised between the absorbent core and the at least one fluid acquisition/distribution layer, and are positioned on opposing sides of the longitudinal axis and/or the transverse axis of the absorbent article.

Topsheet

The topsheet is compliant, soft feeling, and non-irritating to the wearer's skin. The topsheet also can be elastically stretchable in one or two directions. Further, the topsheet is preferably liquid pervious permitting body fluids to readily penetrate through its thickness.

A suitable topsheet can be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. Suitable nonwoven materials/layers include fibrous nonwoven materials/layers formed by a carding process or a spunbond process or meltblown process whereby molten polymeric material is extruded through a die, attenuated to lengthen the extruded polymer into fibers and decrease the diameter thereof and is subsequently deposited on a forming surface. Methods of forming such nonwoven materials/layers are known to those skilled in the art. Polymeric materials suitable for use in forming such fibrous nonwoven materials/layers include polyolefins such as polyethylene and polypropylene, polyesters, nylons, ethylene vinyl acetate, ethylene methacrylate, copolymers of the above materials, block copolymers such as A-B-A block copolymers of styrene and butadiene, and the like.

Apertured formed films are especially preferred for the topsheet because they are pervious to body exudates and yet non-absorbent and have a reduced tendency to allow fluids to pass back through and rewet the wearer's skin. Thus, the surface of the formed film that is in contact with the body remains dry, thereby reducing body soiling and creating a more comfortable feel for the wearer. Suitable formed films are described in U.S. Pat. Nos. 3,929,135, 4,324,246, 4,342, 314, 4,463,045; and 5,006,394. Particularly preferred microapertured formed film topsheets are disclosed in U.S. Pat. Nos. 4,609,518 and 4,629,643. A preferred topsheet for the present invention is the apertured formed film described in one or more of the above patents and marketed on sanitary napkins by The Procter & Gamble Company of Cincinnati, Ohio as "DRI-WEAVE." The body surface of the formed film topsheet can be hydrophilic so as to help liquid to transfer through the topsheet faster than if the body surface was not hydrophilic. In a preferred embodiment, surfactant is incorporated into the polymeric materials of the formed film topsheet such as is described in U.S. patent application Ser. No. 07/794,745, filed on Nov. 19, 1991. Alternatively, the body surface of the topsheet can be made hydrophilic by treating it with a surfactant such as is described in the above referenced U.S. Pat. No. 4,950,254.

In yet an embodiment herein the topsheet is used together with an outer layer being directed towards the wearer surface. Such an outer layer is disposed onto the topsheet in a discontinuous way so that at least the region where liquid is expected to be discharged onto the absorbent article is free of the outer layer. Indeed, it is particularly preferred that the topsheet be a so-called hybrid topsheet in which the wearer contacting surface is provided in its longitudinal center by an apertured polymeric film or nonwoven while a region not including the center is provided with a non-woven such as e.g. the high loft non-woven or other non-woven which does provide particularly skin friendliness. Such hybrid topsheets have been disclosed in EPA-523 683, EP-A-523 719, EP-A-612 233, or EP-A-766 953.

Backsheet

The backsheet prevents the liquids absorbed and contained in the absorbent element from wetting articles that contact the absorbent article such as pants, pajamas and undergarments. The backsheet is preferably impervious to liquids like body fluids and is preferably manufactured from a thin plastic film, although other flexible liquid impervious materials can also be used. The backsheet needs to be compliant and will readily conform to the general shape and contours of the human body. The backsheet also can have characteristics allowing it to elastically stretch in one or two directions.

The backsheet can comprise a woven or nonwoven material, polymeric films such as thermoplastic films of polyethylene or polypropylene, or composite materials such as a film-coated nonwoven material.

Exemplary polyethylene films are manufactured by Clopay Corporation of Cincinnati, Ohio, under the designation P18-0401 and by Ethyl Corporation, Visqueen Division, of Terre Haute, Indiana, under the designation XP-39385. The backsheet is preferably embossed and/or matte finished to provide a more clothlike appearance.

The backsheet typically extends across the whole of the absorbent element and can extend into and form part of or all of the preferred sideflaps, side wrapping elements or wings if such elements are present.

In addition to the prevention of liquid transport through the backsheet, the backsheet is preferably breathable. Hence the backsheet also permits the transfer of water vapor and preferably both water vapor and air through it and thus allows reduction of humid and occlusive environment on the skin contacted with the article. Advantageously the articles of the present invention, when preferably provided with a breathable backsheet, exhibit outstanding dry feeling both in dry and wet conditions and hence further enhanced comfort.

Suitable breathable backsheets for use herein include all breathable backsheets known in the art. Suitable for use herein are single layer breathable backsheets which are breathable and impervious to liquids or dual layer backsheets, which in combination provide both breathability and liquid imperviousness.

Suitable single layer breathable backsheets for use herein include those described for example in GB A 2184389, GB A 2184390, GB A 2184391, U.S. Pat. Nos. 4,591,523, 3,989, 867, 3,156,242 and WO 97/24097.

Suitable apertured formed films for breathable backsheets include films which have discrete apertures which extend beyond the horizontal plane of the garment facing surface of the layer towards the core thereby forming protuberances. The protuberances have an orifice located at their terminating ends. Preferably said protuberances are of a funnel shape, similar to those described in U.S. Pat. No. 3,929,135. Preferably said apertured preformed films are uni directional such that they have at least substantially, if not complete one directional fluid transport towards the absorbent element. Suitable macroscopically expanded films for use herein include films as described in for example in U.S. Pat. No. 637,819, 4,591, 523, 4,637,819 and 4,591,523.

Suitable monolithic films for breathable backsheets include Hytrel™, available from DuPont Corporation, USA, and other such materials as described in Index 93 Congress, Session 7A "Adding value to Nonwovens", J-C. Cardinal and Y. Trouilhet, DuPont de Nemours International S.A., Switzerland. Monolithic films including monolithic compositions such as those disclosed in patent applications WO 99/64077 and WO 99/64505 can also be used for breathable backsheets.

Suitable dual layer breathable backsheets for use herein are made of a first and a second layer. The first layer is positioned between the garment facing surface of the absorbent element and the wearer facing surface of the second layer/outer layer. It is oriented such that it retards or prevents liquid from passing from the absorbent element towards the outside while allowing free air flow and water vapor through it. The second layer provides water vapor and air permeability so as to support breathability of the article. In addition to water vapor permeability the air permeability is desirable in order to further improve the comfort benefit from the breathability of the article. Such a first layer provides air and water vapor permeability by being apertured. Preferably this layer is made in accordance with the U.S. Pat. No. 5,591,510 or PCT WO 97/03818, WO 97/03795. In particular, this layer comprises a polymeric film having capillaries. Using a monolithic polymer film as the material for the first layer provides water vapor permeability even under stress conditions. While the apertures provide air permeability during "leakage safe" situations but close the capillaries under stress conditions the monolithic material maintains water vapor permeability in such a case. Preferred breathable monolithic film materials for use herein are those having a high vapor exchange.

In one embodiment herein the backsheet is made of a first layer of a resilient, three dimensional web which consists of a liquid impervious polymeric film having apertures forming capillaries which are not perpendicular to the plane of the film but are disposed at an angle of less than 90° relative to the plane of the film, and a second breathable layer (outer layer) of a porous web which is a fibrous nonwoven composite web of a meltblown nonwoven layer made from synthetic fibers having a basis weight of less than 28, preferably less than 13 g/m$^2$ and of a spunbonded nonwoven layer made from synthetic fibers.

The backsheet typically forms the garment facing surface on which the panty fastening adhesive is placed. Panty-fastening-adhesives can comprise any adhesive or glue used in the art for such purposes with pressure-sensitive adhesives being preferred.

Absorbent Core

The absorbent core, which is disposed between the topsheet and the backsheet, absorbs and retains bodily fluids that have penetrated the topsheet after discharge by a wearer. The absorbent core may be any absorbent means which is capable of absorbing or retaining bodily liquids (e.g., menses and/or urine). The absorbent core may be manufactured in a wide variety of sizes and shapes (e.g., rectangular, oval, hourglass, dog bone, asymmetric, etc.) and from a wide variety of liquid-absorbent materials commonly used in sanitary napkins and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combinations of materials, or mixtures of these, such as for example laminated structures comprising outer fibrous layers and particles of superabsorbent polymers comprised therebetween, or composite structures comprising any of the above structures and one or more further layers below or above it, e.g. fibrous layers such as for example spunlaced nonwoven layers. The configuration and construction of the absorbent core may also be varied (e.g., the absorbent core may have varying caliper zones (e.g., profiled so as to be thicker in the center), hydrophilic gradients, superabsorbent gradients, or lower density and lower average basis weight acquisition zones; or may comprise one or more layers or structures). The total absorbent capacity of the absorbent core should, however, be compatible with the design loading and the intended use of the sanitary napkin. Further, the size and absorbent capacity of the absorbent core may be varied to accommodate different uses such as incontinence pads, pantiliners, regular sanitary napkins, or overnight sanitary napkins. Exemplary absorbent structures suitable for use as the absorbent core of the present invention are described in U.S. Pat. No. 4,950,264 issued to Osborn on Aug. 21, 1990; U.S. Pat. No. 4,610,678 issued to Weisman et al. on Sep. 9, 1986; U.S. Pat. No. 4,834,735 issued to Alemany et al. on May 30, 1989; European Patent Application No. 0 198 683, The Procter & Gamble Company, published Oct. 22, 1986 in the name of Duenk, et al.; and U.S. Pat. No. 5,009,653 issued to Osborn, III, on Apr. 23, 1991.

Optionally, the absorbent articles of the present invention can comprise all those components typical for the intended product use. For example absorbent articles such as sanitary napkins and pantiliners can comprise components such as wings in order to improve their positioning and soiling protection performance especially towards the rear end of the article. Such designs are shown for example in EP 130 848 or EP 134 086, Thong liners with wings are shown in U.S. design 394,503, UK designs 2,076,491 and 2,087,071 as well as internationally filed industrial model DM 045544, filed under the Hague Agreement, registered on Oct. 21, 1998.

Wings can be provided as separate pieces and be attached to the article, typically a pantiliner or a sanitary napkin, or they can be integral with the materials of the absorbent articles, e.g. by being integral extension of the topsheet, the backsheet or a combination thereof. If the wings are attached then they can be attached in a basic outward pointing position or already be predisposed towards their in-use position, i.e. towards the longitudinal centerline.

Fluid Acquisition/Distribution Layer

The fluid acquisition/distribution layer serves primarily the function of improving acquisition of body fluids and subsequent wicking and diffusion within its structure.

There are several reasons why the improved wicking of body fluids is important, including providing a more even distribution of the body fluids throughout the absorbent core and for example allowing the absorbent article to be made relatively thin. The wicking referred to herein may encompass the transportation of liquids in one, two or all directions, i.e., in the x-y plane and/or in the z-direction. The fluid acquisition/distribution layer may comprise several different materials including nonwoven or woven webs of synthetic fibers including polyester, polypropylene, or polyethylene; natural fibers including cotton or cellulose; blends of synthetic and natural fibers; or any equivalent materials or combinations of materials.

The fluid acquisition/distribution layer can be comprised between the topsheet and the absorbent core, therefore typically acting as a secondary topsheet, and alternatively or in addition, between the absorbent core and the backsheet. In the first case the fluid acquisition/distribution layer is meant to first acquire the fluid directly through the topsheet, and owing to its capillary structure to evenly and effectively distribute it within its thickness in a larger area, before releasing it to the underlying absorbent core. A fluid acquisition/distribution layer positioned below the absorbent core, as an alternative to a secondary topsheet type fluid acquisition/distribution layer, or in addition thereto, is meant to rapidly acquire and spread the fluid which can pass through the absorbent core before it is effectively diffused and absorbed therein. This may happen for example with thin absorbent articles having a thin absorbent core, e.g. constituted by a laminate structure with outer fibrous layers and particles of absorbent gelling material distributed therebetween, in the event of a sudden surge of a relatively high amount of fluid released from the body. The fluid reaches the thin absorbent core and, if it cannot be completely acquired and absorbed therein, can at least partially pass through the core and reach its garment facing surface. An underlying adjacent fluid acquisition/distribution layer can therefore acquire and effectively distribute this fluid, making it available for a subsequent absorption through a larger area of the garment facing surface of the absorbent core. Multiple fluid acquisition/distribution layers can be also used in an absorbent article, for example one comprised between the core and the topsheet, and one comprised between the core and the backsheet, or also two or more fluid acquisition/distribution layers superimposed to one another to form a multilayer structure. Multiple fluid acquisition/distribution layers can also comprise different, not superimposed layers, for example two separate narrower layers, each one associated to a respective edge barrier element.

Examples of absorbent articles, namely sanitary napkins having a secondary topsheet type fluid acquisition/distribution layer are more fully described in U.S. Pat. No. 4,950,264. Any material known to those skilled in the art might be used herein for the at least one fluid acquisition/distribution layer, including but not limited to fibrous nonwoven or woven materials, made of natural or synthetic fibres like polyolefins or cellulose, such as for example a spunlaced nonwoven layer. When the fluid acquisition/distribution layer is in the form of a secondary topsheet, can be preferably an air laid tissue having a basis weight of about 35 grams per square meter (gsm). A suitable material is available from Merfin Hygiene Products Ltd., Delta, BC, Canada. Alternative nonwoven materials suitable for forming the secondary topsheet type fluid acquisition/distribution layer include a nonwoven fabric of spunbonded polypropylene fibers available from the Fiberweb Corporation of Simpsonville, S.C. under the tradename CELESTRA and a nonwoven fabric formed of bicomponent fibers which have a polyethylene sheath and a polyurethane core, which is available from the Havix Company, of Japan, as S2416.

Edge Barrier Elements

Figure 1:
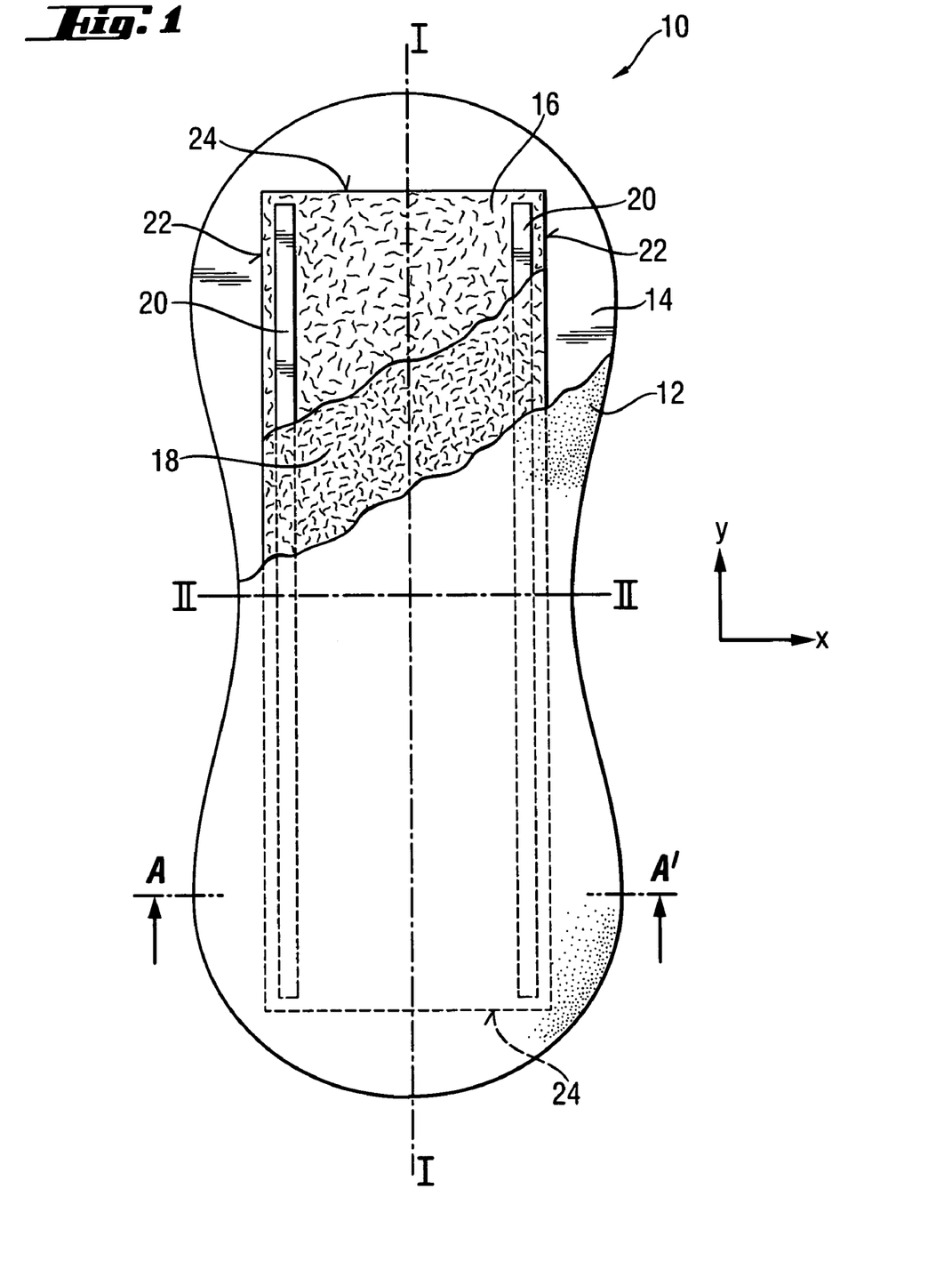
FIG. 1 shows a top plan view of the garment facing surface of a sanitary napkin according to the present invention having edge barrier elements made of a liquid absorbent thermoplastic composition as described herein.
Figure 2:
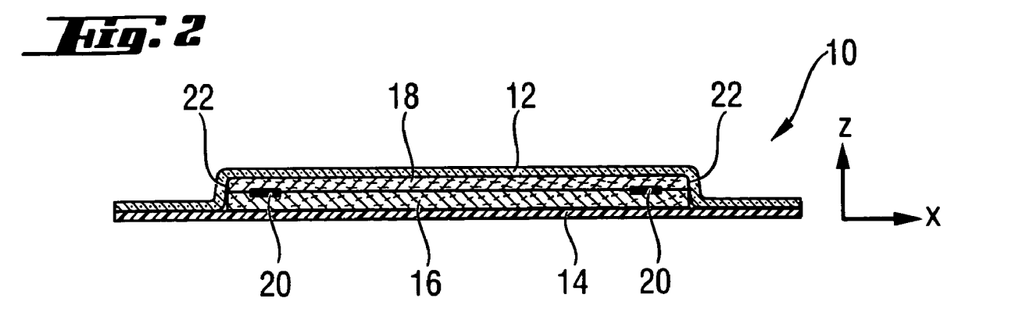
FIG. 2 is a transverse section of the sanitary napkin of FIG. 1 taken through line A-A'.

The edge barrier elements, distinct form the absorbent core and in addition thereto, constitute an essential feature of the absorbent article of the present invention, which is described below with reference to a sanitary napkin, as illustrated in FIGS. 1 and 2.

FIG. 1 shows a top plan view of a sanitary napkin 10 according to a preferred embodiment of the present invention, with some of the elements forming the article partially torn away in order to more clearly show the article structure. The sanitary napkin 10 comprises a topsheet 12, a backsheet 14, and an absorbent core 16 comprised between the topsheet and the backsheet. The sanitary napkin 10 further comprises a fluid acquisition/distribution layer 18, disposed between the absorbent core 16 and the topsheet 12. A first and a second edge barrier element 20, distinct from the absorbent core 16, are positioned on opposing sides of the longitudinal axis I- I, namely each barrier element 20 is in form of a continuous narrow stripe running substantially along the entire respective longitudinal edge margin 22 of the core 16, and parallel thereto. The edge barrier elements 20 according to the present invention comprise, and typically are constituted of, a liquid absorbing thermoplastic composition which comprises a polymeric base material having particles of water-insoluble water-swellable absorbent material dispersed therein, also referred to as particles of superabsorbent material, or of absorbent gelling material (AGM).

The edge barrier elements 20 are comprised between the absorbent core 16 and the fluid acquisition/distribution layer 18, which in the embodiment of the present invention illustrated in FIGS. 1 and 2 substantially constitutes a secondary topsheet, being positioned between the topsheet 12 and the absorbent core 16.

The edge barrier elements 20 are capable of intercepting body fluids before they reach the edges of the absorbent core 16, and according to the present invention they provide a better and more effective containment and leak prevention action, together with a better overall fluid acquisition and handling capacity of the entire absorbent article, by working in combination with the layers, namely the absorbent core 16 and the fluid acquisition/distribution layer 18, between which they are comprised.

According to the known mechanism, the fluid acquisition/distribution layer 18, upon first contact with fluid received directly through the topsheet 12, effectively diffuses and spreads the fluid in both x and y directions, in addition to directly through its thickness, i.e. in z-direction, and makes it available to the underlying absorbent core 16 over a larger area for absorption and retention. The fluid can also tend to partially diffuse, at least in the initial stage of the absorption process, over and along the outer body facing surface of the absorbent core, for example in case of very thin core structures, such as for example laminated structures with two outer fibrous layers capable of rapidly diffusing fluid and particles of superabsorbent material distributed therebetween. This effective distribution of the fluid over a larger area within the layers, typically fibrous layers, comprised in the absorbent article, while beneficial to the overall performance of the article, taking advantage more effectively of the absorbent capacity of the absorbent core, can bring at least some fluid towards the edges of the absorbent core, typically the longitudinal edge margins 22 of the absorbent core, which are usually closer to the area first reached by the fluid, but also the transverse edge margins 24. However, the presence of the side edge barrier elements 20 comprised between the fluid acquisition/distribution layer 18 and the absorbent core 16 effectively intercepts the fluid and prevents it from reaching the edge margins of the core, typically the longitudinal edge margins 22 in the embodiment of FIGS. 1 and 2.

Without being bound to any theory, it is speculated that the presence of edge barrier elements 20 between two layers, typically fibrous layers, which are respectively meant to receive, diffuse, and absorb fluid, provides a synergistic effect combining the fluid acquisition/distribution, and absorption capability of these layers, with the fluid intercepting capability of the edge barrier elements contained therebetween. In other words, the fluid is very effectively diffused by wicking within the fluid acquisition/distribution layer, and the adjacent outer surface of the absorbent core, and namely at the interface between the said fluid acquisition/distribution layer and the absorbent core, which are in fluid communication with each other. At the same time, the edge barrier elements comprised between the two adjacent layers provide effective barrier action by intercepting the fluid before it reaches the edge margins of the absorbent core.

According to an alternative preferred embodiment of the present invention, which will be illustrated in more detail further on with reference to the specific embodiment of FIG. 3, a fluid acquisition distribution layer can be comprised below the absorbent core, i.e. between the core and the backsheet, as an alternative, or in addition, to the fluid acquisition distribution layer 18 positioned as a secondary topsheet as illustrated in FIGS. 1 and 2. The same mechanism described above also applies to the combination of the fluid acquisition/distribution layer below the absorbent core, with the edge barrier elements comprised between them. This is particularly useful in case of thin absorbent cores, for example comprising a laminated structure with two outer fibrous layers and particles of superabsorbent material therebetween. In certain conditions the fluid can in fact directly pass through the absorbent core before being effectively absorbed within its structure, for example in case of repeated discharges of relatively high amounts of fluids, such as for example in a sanitary napkin worn during the initial period of particularly heavy menstrual flow. The combination of the fluid acquisition/distribution layer below the absorbent core, with the edge barrier elements between the two, ensures an effective handling of the excess fluid, which is diffused through the fluid acquisition/distribution layer and made available for subsequent absorption within the absorbent core over a larger area. The presence of the edge barrier elements at the same time prevents leakage form the core edge margins.

Each edge barrier element in the absorbent article of the present invention can be preferably constituted by more than one stripe of liquid absorbing thermoplastic composition. For example each edge barrier element can comprise two or more separate stripes, typically parallel to one another and also equidistant to one another in case of three or more stripes, thus providing an improved barrier effect for intercepting fluids. Each stripe comprised in the edge barrier element of the present invention can be continuous, or alternatively discontinuous. Multiple identical stripes for a single edge barrier element, running parallel to one another, are preferred since they provide a more efficient barrier effect for intercepting fluids, compared to a single stripe typically having the same length and using the same amount of liquid absorbing thermoplastic material as the multiple stripes in combination.

In the embodiment illustrated in FIG. 1 the absorbent core 16 has a substantially rectangular shape, and each edge barrier element 20 comprises a rectilinear stripe of liquid absorbing thermoplastic composition which is parallel to the respective longitudinal edge margin 22 of the core 16. However, the absorbent article according to the present invention can also comprise alternative configurations in which the edge barrier elements, each one comprising one or more stripes, are not parallel to the respective longitudinal edge margins of the absorbent core. As non limiting examples, these alternative configurations comprise the embodiment where the absorbent core is not rectangular, but differently shaped, as it is known in the art, for example hourglass shaped, and the edge barrier elements are rectilinear, and parallel to the longitudinal axis I-I of the article, or alternatively parallel to the longitudinal edge margins of the core, as shown e.g. in FIG. 4, or also curved along a different curvature compared to the longitudinal edge margins of the core. Alternatively, curved edge barrier elements can be combined with a rectangular core.

Figure 4:
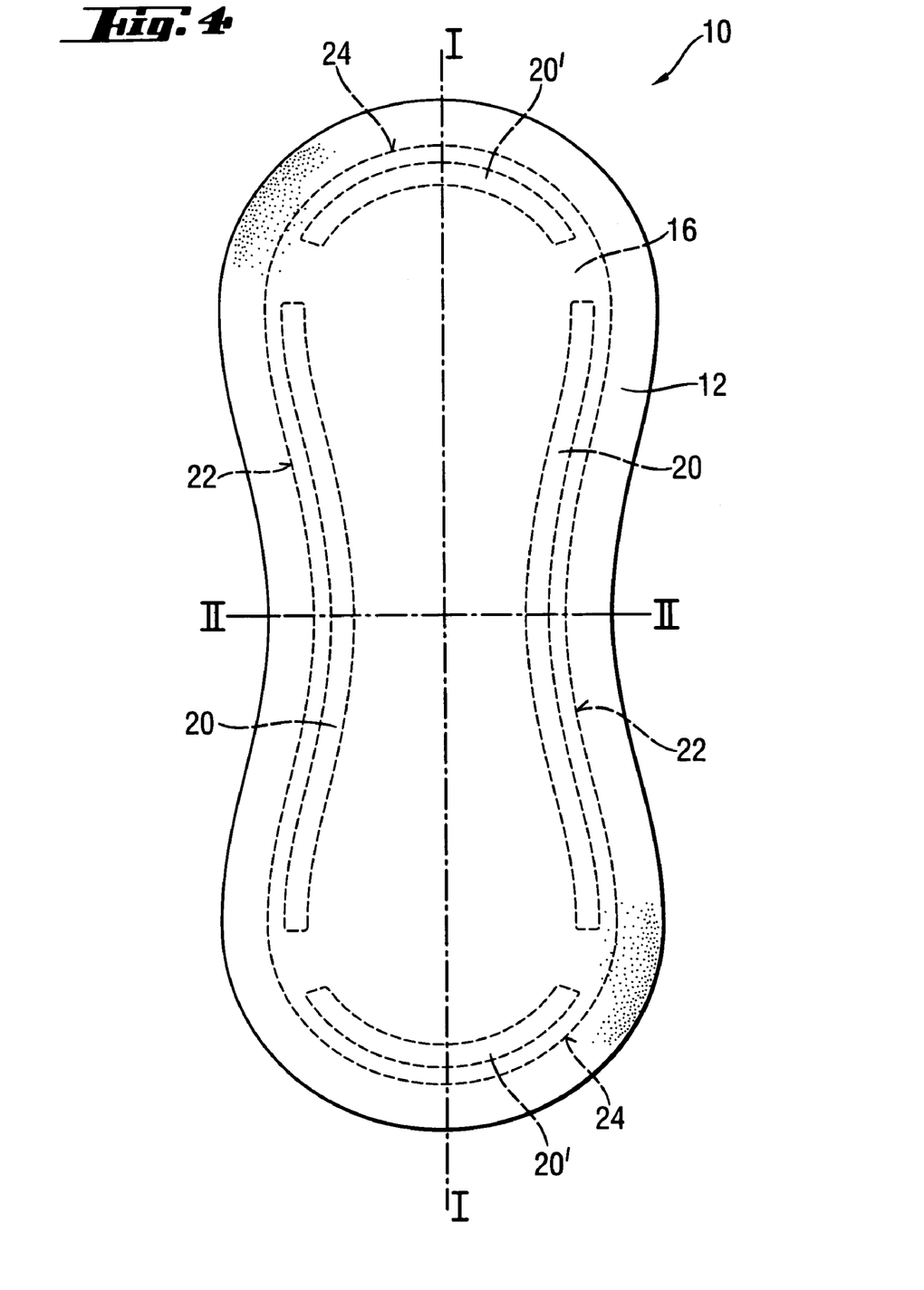
FIG. 4 is a schematic top plan view of a sanitary napkin according to an alternative embodiment of the present invention.

The absorbent article according to the present invention can also comprise, as an alternative to, or in addition to the first and second edge barrier elements positioned on opposing sides of the longitudinal axis I-I of the article, edge barrier elements positioned on opposing sides of the transverse axis II-II of the article. FIG. 4 shows an embodiment of the present invention comprising first and second edge barrier elements 20 positioned on opposing sides of the longitudinal axis I-I, which in this case are also parallel to the longitudinal edge margins 22 of the absorbent core 16, and further first and second edge barrier elements 20' positioned on opposing sides of the transverse axis II-II of the article, also substantially parallel to the transverse side edges 24 of the absorbent core 16. Of course same considerations apply to the edge barrier elements 20', which can also be constituted by a single or multiple stripes of the liquid absorbing thermoplastic composition, each stripe being continuous or alternatively discontinuous. Edge barrier elements 20' can be rectilinear or curvilinear, parallel to the respective transverse edge margin of the absorbent core, or not parallel thereto.

According to a further alternative embodiment of the present invention, edge barrier elements 20 and edge barrier elements 20' can be comprised in a continuous, single or multiple, stripe running all the way along the longitudinal edge margins 22 and the transverse edge margins 24 of the absorbent core, optionally parallel thereto.

Although in the embodiment of FIGS. 1 and 2 the absorbent core 16 and the at least one fluid acquisition/distribution layer 18 are coterminous, according to alternative embodiments of the present invention they can have different shape and extension, provided the at least first and second edge barrier elements 20 are positioned at least partially between the absorbent core and the at least one fluid acquisition/distribution layer.

According to a further alternative preferred embodiment of the present invention, an edge barrier element, preferably both the at least first and second edge barrier element, laterally extends partially outside of the respective longitudinal edge margins of the absorbent core and/or of the fluid acquisition/distribution layer. This feature is more preferably comprised in an absorbent article according to the present invention in combination with an absorbent core and a fluid acquisition/distribution layer having different widths. For example, preferred embodiments comprise edge barrier elements extending laterally outside of the respective longitudinal edge margins of the absorbent core only, in combination with a fluid acquisition/distribution layer wider than the absorbent core, and vice versa edge barrier elements extending laterally outside of the respective longitudinal edge margins of the fluid acquisition/distribution layer only are combined with an absorbent core which is wider than the fluid acquisition/distribution layer. Preferably each of said at least first and second edge barrier elements laterally extends along its entire length partially outside of the respective longitudinal edge margin of the absorbent core and/or of the fluid acquisition/distribution layer.

The features above can provide further protection against leakage also toward fluid that may possibly leave a longitudinal edge margin of the absorbent core and/or of the fluid acquisition/distribution layer, for example being squeezed out during particularly heavy wearing conditions, combining heavy fluid load of the core and stress conditions due e.g. to the user's movements.

Figure 3:
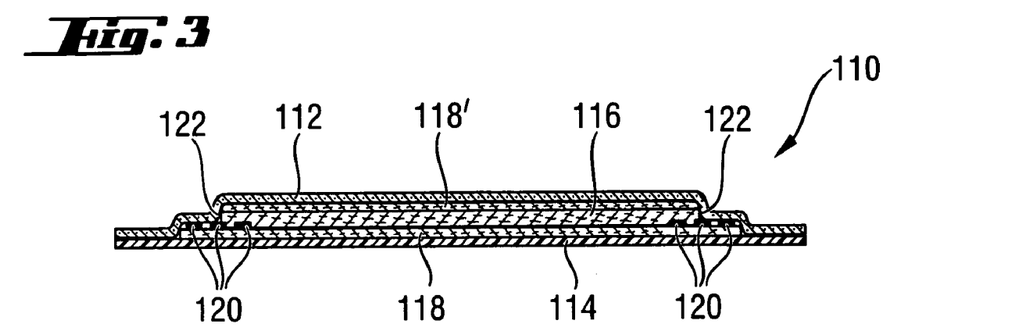
FIG. 3 is a transverse section of a sanitary napkin according to an alternative preferred embodiment of the present invention.

For example, according to a preferred alternative embodiment of the present invention illustrated in FIG. 3, the absorbent article 110 comprises a fluid acquisition/distribution layer 118 positioned between the absorbent core 116 and the backsheet 114, wherein the fluid acquisition/distribution layer 118 is wider then the overlying absorbent core 116. The absorbent article 110 further comprises a second fluid acquisition/distribution layer 118', positioned between the topsheet 112 and the absorbent core 116, hence acting a secondary topsheet and having in the illustrated embodiment the same width as the absorbent core 116.

In the illustrated preferred embodiment, each edge barrier element 120 is constituted by three identical stripes of the liquid absorbing thermoplastic composition, equidistant to one another, and also parallel to one another and to the respective longitudinal edge margin 122 of the absorbent core 116. Each edge barrier element 120 is positioned entirely over the fluid acquisition/distribution layer 118, wider than the core 116, and partially extends along its entire length laterally outside of the respective longitudinal edge margin 122 of the absorbent core.

The embodiment of FIG. 3 can be particularly preferred for absorbent articles with high density, typically thin, absorbent cores, which have particularly good distribution/wicking capacity both in the x-y plane and in z direction. Fluid can be efficiently distributed through the core, as well as reach the underlying layer directly through the core thickness. Fluid can hence flow along a dual path, i.e. reach the core edges quickly within the core itself, typically the longitudinal edge margins 122, being then blocked by the edge barrier elements 120, and further by their respective portions extending partially outside of the longitudinal edge margins 122, but preferably still positioned onto the fluid acquisition/distribution layer 118, as shown in the embodiment of FIG. 3. At the same time fluid is also acquired by the underlying fluid acquisition/ distribution layer 118 through the core thickness and further distributed along the garment facing surface of the core, being blocked by the edge barriers elements 120 as well before reaching the longitudinal edge margins of the fluid acquisition/distribution layer 118.

Figure 5:
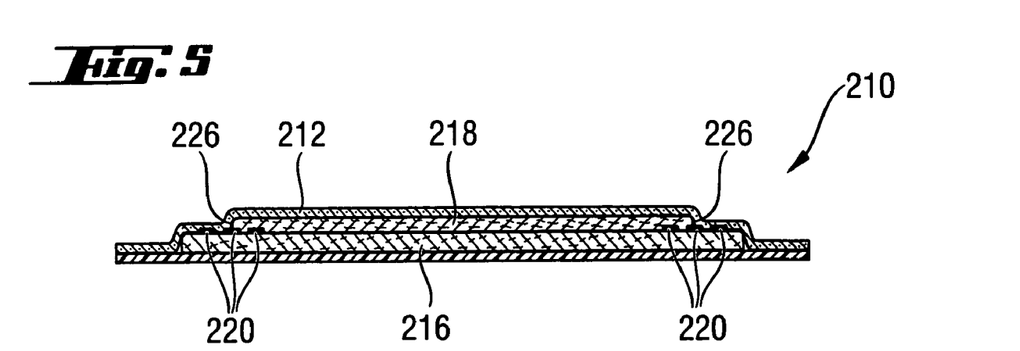
FIG. 5 is a transverse section of a sanitary napkin similar to that of FIG. 3, and according to a further alternative embodiment of the present invention.

An alternative preferred embodiment is illustrated in FIG. 5, which shows an absorbent article 210 similar to that of FIG. 3, but with a fluid acquisition/distribution layer 218 comprises between the topsheet 212 and the absorbent core 216, and being narrower than the latter. Each edge barrier element 220, constituted by three stripes of the liquid absorbing thermoplastic composition having the same arrangement already described with reference to FIG. 3, is positioned entirely over the core 216, which is wider than the fluid acquisition/distribution layer 218, and partially extends along its entire length laterally outside of the respective longitudinal edge margin 226 of the fluid acquisition/distribution layer 218.

The embodiment of FIG. 5 can be particularly preferred for absorbent articles having low density, typically thick, fluffy cores with a relatively low fluid distribution capacity. The fluid is rapidly and efficiently distributed mainly within the fluid acquisition/distribution layer 218, and spread over the body facing surface of the core 216. The fluid can actually reach the very ends of the fluid acquisition/distribution layer 218, particularly its longitudinal edge margins 226, but side leakage is prevented by the edge barrier elements 220 which extend laterally further as shown in FIG. 5, in combination with the portions of the core 216 also extending laterally outside the longitudinal edge margins 226 of the fluid acquisition/distribution layer 218.

Alternatively, for the two embodiments of FIGS. 3 and 5, a single wider stripe can be used for each edge barrier element, with the same arrangement relative to the respective longitudinal edge margin of the fluid acquisition/distribution layer and of the core.

As a less preferred alternative to the multiple stripes constituting the edge barrier elements in the embodiments above, each edge barrier element 120, 220 can be constituted by a single stripe of the liquid absorbing thermoplastic composition having a suitable width, and being positioned between the absorbent core and the at least one fluid acquisition/distribution layer, such that a portion of the edge barrier element laterally extends partially outside the respective longitudinal edge margin 122, 226 of the core 116 or of the fluid acquisition/distribution layer 218.

In general, according to the present invention, providing that the at least first and second edge barrier elements are positioned at least partially between the absorbent core and the at least one fluid acquisition/distribution layer does not exclude that additional elements or layers are also comprised between the core and the fluid acquisition/distribution layer, typically further fibrous layers, in addition to the edge barrier elements. For example, a further absorbent layer can be comprised between the core and the fluid acquisition/distribution layer, thus ultimately forming a layered structure comprising, e.g. from top to bottom, a fluid acquisition/distribution layer, a first absorbent layer, which could constitute e.g. a primary core element, at least first and second edge barrier elements, and the absorbent core, which could constitute a secondary core element in this alternative embodiment of the present invention.

According to a further alternative preferred embodiment of the present invention, an absorbent article can also comprise an upper fluid acquisition/distribution layer positioned between the topsheet and the absorbent core, and a lower fluid acquisition/distribution layer positioned between the absorbent core and the backsheet, wherein at least first and second edge barrier elements are positioned between the upper fluid acquisition/distribution layer and the core, and further at least first and second edge barrier elements are positioned between the lower fluid acquisition/distribution layer and the absorbent core. Such a configuration can provide an absorbent article with a further enhanced fluid management capability combined with edge leakage prevention.

Preferably the at least first and second edge barrier elements can be configured to overall cover an area not more than 60 cm$^2$, more preferably from 2 cm$^2$ to 60 cm$^2$, even more preferably from 10 cm$^2$ to 40 cm$^2$, most preferably from 20 cm$^2$ to 30 cm$^2$. Preferably the area of the body facing surface or of the garment facing surface of the absorbent core covered by the edge barrier elements constitutes not more than 35%, more preferably from 2% to 32%, even more preferably from 5% to 30%, most preferably from 15% to 25%, of the total area of the respective surface of the core.

Each edge barrier element is preferably constituted by a continuous stripe, more preferably by multiple continuous stripes being parallel to one another, each stripe having a width comprised from 0.1 mm to 20 mm, preferably from 0.5 mm to 15 mm, more preferably from 1 mm to 10 mm. Multiple stripes preferably constituting an edge barrier element are separated from each other by a distance of at least 0.1 mm, preferably from 0.5 to 10 mm, more preferably from 1 to 5 mm, and most preferably from 1.2 to 4 mm to provide the desired improved barrier effect for intercepting fluids.

The distance between the at least first and second edge barrier element positioned on opposing sides of the longitudinal and/or of the transverse axis of the absorbent article is preferably at least 20%, preferably at least 25%, of the minimum width of the absorbent core for edge barrier elements positioned on opposing sides of the longitudinal axis, and at least 20%, preferably at least 25%, of the length of the absorbent core measured along the longitudinal axis, for edge barrier elements positioned on opposing sides of the transverse axis. In any case the minimum distance between first and second edge barrier elements positioned on opposing sides of the longitudinal and/or of the transverse axis must be at least 10 mm, preferably at least 15 mm, more preferably at least 20 mm.

The liquid absorbing thermoplastic composition of the edge barrier elements comprises particles of water-insoluble water-swellable absorbent material dispersed homogeneously or non-homogeneously in a thermoplastic polymeric base material, as the suitable carrier.

Water-insoluble but water-swellable absorbent materials or absorbent gelling materials are usually referred to as "hydrogels", "super absorbent", "absorbent gelling" materials. Absorbent gelling materials are those materials that, upon contact with aqueous fluids, especially aqueous body fluids, imbibe such fluids and thus form hydrogels. These absorbent gelling materials are typically capable of absorbing large quantities of aqueous body fluids, and are further capable of retaining such absorbed fluids under moderate pressures. These absorbent gelling materials are typically in the form of discrete, non fibrous particles, even if super absorbent in fiber form are known.

Any commercially available super absorbent material in particle form is suitable for the present invention. Suitable absorbent gelling materials for use herein will most often comprise a substantially water-insoluble, slightly crosslinked, partially or fully neutralized, polymeric gelling material. This material forms a hydrogel upon contact with water. Such polymer materials can be prepared from polymerizable, unsaturated, acid-containing monomers.

It is preferable that the particle size of the absorbent material used herein in dry state is below 150 micrometers, more preferably below 50 micrometers and most preferably from 40 to 10 micrometers. Small particle sizes are preferred herein as this results in optimum performance and processability for adhering the thermoplastic composition to the desired substrate. "Particle size" as used herein means the weighted average of the smallest dimension of the individual particles. Highly preferred water insoluble water swellable materials for use herein have a substantially angle-lacking shape and preferably have a spherical shape. Suitable commercially available absorbent gelling material is for example Aquakeep® 10SH-NF, available from Sumitomo Seika, having an average particle size of between 20 µm and 30 µm.

It is preferable that the water insoluble water swellable absorbent material is present in an amount from 1% to 95%, preferably from 10% to 90%, more preferably from 30% to 70% and most preferably from 40% to 60% by weight of the total liquid absorbent thermoplastic composition.

The liquid absorbent thermoplastic composition for use herein besides the absorbent material further comprises as an essential element a polymeric base material typically at a level from 5% to 99%, preferably 10% to 90%, more preferably from 30% to 70%, most preferably from 40% to 60% by weight of the liquid absorbent thermoplastic composition.

Any polymeric base material known to the skilled person and conventionally used in the construction of absorbent articles, such as feminine care absorbent articles (e.g. sanitary napkins, panty liners or incontinence articles) or baby care absorbent articles (e.g. diapers) can be used herein. The polymeric base materials for use herein comprise thermoplastic polymers as an essential element. Thermoplastic polymer or mixtures of polymers are present in amounts typically ranging from about 5% to 99%, preferably 10% to 90%, more preferably from 30% to 70%, most preferably from 40% to 60% with respect to the total weight of the thermoplastic polymeric base material.

Liquid absorbing thermoplastic compositions comprising particles of superabsorbent material are already known in the art, and can be used to provide the edge barrier elements in the absorbent articles of the present invention. For example, materials described in patent applications WO 98/27559 and WO 99/57201 can be used in the present invention.

A particularly preferred liquid absorbing thermoplastic composition comprising particles of superabsorbent material is described in patent application WO 03/49777. This application discloses highly preferred thermoplastic polymeric base materials for use in the liquid absorbent thermoplastic compositions to be applied in the absorbent articles of the present invention, which have a water absorption capacity at least greater than 30%, preferably greater than 40%, more preferably greater than 60% and most preferably greater than 90%, when measured according to the Water Absorption Test described herein in accordance with ASTM D 570-81, on a film 200 µm thick. The intrinsic absorbency of the polymeric base material/matrix allows for a more effective diffusion of the body fluid within the matrix and, consequently, for a better spreading of the body fluid which can reach a greater number of absorbent material particles which in turn give rise to a better utilization of the absorbent material.

Highly preferred liquid absorbent thermoplastic compositions described in WO 03/49777 are those showing good integrity in wet state and hence having a tensile strength in wet state which is at least 20%, preferably at least 40%, and more preferably 60% of the tensile strength of said composition in dry state. Said tensile strengths are evaluated according to the Tensile Strength Test described herein. It should be appreciated that by selecting a thermoplastic base material, in the liquid absorbent thermoplastic composition herein having a higher value of water absorption, the absorbent composition will have better liquid absorption/handling characteristics, while not compromising on tensile strength in wet state. Indeed such absorbent composition will remain substantially intact and have sufficient tensile strength for its intended use, also upon liquid absorption.

Indeed the highly preferred liquid absorbent thermoplastic compositions for use herein offer improved mechanical and absorbent properties. Without being bound by theory it is believed that the intrinsic absorbency of the matrix allows the body fluid to be acquired and diffused within the matrix thus permitting fluid contact with the absorbent material contained in the matrix and their swelling, without the necessity of having a matrix of low cohesive strength but with a matrix which remains substantially intact and having sufficient strength upon fluid absorption.

The absorbent in particle form or mixture thereof are blended with the polymeric base material in any known manner to provide the liquid absorbent thermoplastic composition for use herein. For example, by first melting the thermoplastic polymeric base material and then by adding and mixing the required amount of absorbent material particles. Suitable adhesive processing equipments can be used such as a melt mixer or extruder. Preferably the liquid absorbing thermoplastic compositions for use herein are formulated to have hot melt characteristics so that they can be applied utilizing any know method used for applying hot melt adhesives.

At least at the coating temperature, since the liquid absorbent thermoplastic composition comprises thermoplastic polymeric base materials, it can exhibit adhesive properties on a supportive substrate in order to form a composite structure such that no additional adhesive is required to achieve a permanent attachment of the layers between which the edge barrier elements, and hence the liquid absorbing thermoplastic composition, are comprised, typically at least the absorbent core and a fluid acquisition/distribution layer. However, while hot melt techniques are preferred, any other known method for processing thermoplastic compositions can be used for processing the absorbent compositions in any known form/pattern. Also, any known method for spraying, printing, dotting, coating or foaming thermoplastic compositions can be used as well as extrusion, lamination processes.

Particularly suitable methods for applying the liquid absorbent thermoplastic composition to a substrate is per gravure printing or slot coating. Both methods are particularly suitable for discontinuous application of the thermoplastic composition described herein onto a substrate. A gravure print unit or a slot coater applies the thermoplastic composition in the desired pattern onto a substrate.

Because the absorbent composition is thermoplastic, it allows for hot melt technique applications which in turn increase the versatility of its application in the selected suitable pattern and on different substrates, for example directly onto the absorbent core, or alternatively onto the fluid acquisition/distribution layer.

The liquid absorbing thermoplastic composition can be applied onto the selected substrate in order to form the edge barrier elements with a basis weight from 10 $g/m^2$ to 2000 $g/m^2$, preferably from 50 $g/m^2$ to 1000 $g/m^2$, more preferably from 100 $g/m^2$ to 350 $g/m^2$, said basis weight considered for each single element constituting the edge barrier element, e.g. typically for the single stripe in a multiple stripe edge barrier element.

According to an alternative embodiment of the present invention, a continuous layer of liquid absorbing thermoplastic composition positioned between the absorbent core and at least one fluid acquisition/distribution layer can still provide the absorbent article with the advantage of an improved liquid acquisition, distribution and retention, with less risk of side leakage, although without the presence of edge barrier elements, owing to the synergistic action of the liquid absorbing thermoplastic composition in combination with the two layers, namely the absorbent core and the fluid acquisition/distribution layer, which comprise it therebetween. The layer of liquid absorbing thermoplastic composition can alternatively be not continuous, namely provided in a discontinuous but interconnected pattern. A discontinuous but interconnected pattern comprises single elements of the liquid absorbing thermoplastic composition which are interconnected to one another, such as for example interconnected lines, stripes, dots, circles, squares, etc. connected to one another thus forming a discontinuous layer, i.e. having void areas. An example of an absorbent article according to the present invention is described herein after.

A sanitary napkin similar to that illustrated in FIGS. 1 and 2 comprises, from top to bottom, as the topsheet an apertured polymeric film (CPM RIS coded 1035025 available from Tredegar), as the fluid acquisition/distribution layer a 40 g/m$^2$ BICO thermalbonded carded nonwoven (coded Sawabond 4313 available from Sandler), as the absorbent core a composite air laid structure comprising bicomponent and cellulose fibres, superabsorbent particles, and a binder, as sold by Concert GmbH under the code GH.150.1006, and as the backsheet a polyethylene film manufactured by Clopay Corporation of Cincinnati, Ohio, under the designation P18-0401.

The absorbent core and the fluid acquisition/distribution layer are rectangular and coextensive, and comprise between them first and second edge barrier elements, each running longitudinally substantially along the whole length of the respective common longitudinal edge margin of the core and of the fluid acquisition/distribution layer. Each edge barrier element is constituted by three continuous stripes of a liquid absorbing thermoplastic composition, running parallel to one another, and separated by a distance of 3 mm. Each stripe has a width of 2 mm and comprises the liquid absorbing thermoplastic composition applied with a basis weight of about 300 g/m$^2$. The distance between the innermost stripes of the first and second edge barrier element is 36 mm.

The liquid absorbing thermoplastic composition forming the edge barrier elements has the following composition, forming a hot-melt adhesive:

| | |
|---|---|
| 18% | Estane T5410 from Noveon |
| 17% | PEG E400 from Dow Chemical |
| 1% | Irganox B 225 from Ciba Speciality Chemicals |
| 19% | CR00 (former PM17) from Savare |
| 45% | Aquakeep 10 SH-NF ® from Sumitomo-Seika. |

Estane T5410 is a polyurethane—hydrophilic thermoplastic polymer, PEG E400 is a polyethylene glycol (plasticizer, MW about 400), Irganox B 225 an anti oxidant and CR00 is a commercially available adhesive hotmelt.

While particular embodiments of the present invention have been illustrated and described, it would be obvious to those skilled in the art that various other changes and modifications can be made without departing from the scope of the invention. It is therefore intended to cover in the appended claims all such changes and modifications that are within the scope of this invention.

What is claimed is:

1. An absorbent article having a longitudinal axis and a transverse axis, said absorbent article comprising a topsheet, a backsheet, an absorbent core positioned between said topsheet and said backsheet, and at least a fluid acquisition/distribution layer;
   wherein said absorbent article further comprises at least a first and a second edge barrier element for intercepting fluids, said at least first and second edge barrier element being positioned on opposing sides of said longitudinal axis and/or of said transverse axis;
   wherein said at least first and second edge barrier elements comprising a liquid absorbing thermoplastic composition which comprises a polymeric base material having particles of water-insoluble water-swellable absorbent material dispersed therein;
   wherein said absorbent article further comprises an upper fluid acquisition/distribution layer positioned between said topsheet and said absorbent core, a lower fluid acquisition/distribution layer positioned between said backsheet and said absorbent core, at least a first and a second edge barrier element positioned between said upper fluid acquisition/distribution layer and said core, and at least a first and a second edge barrier element positioned between said lower fluid acquisition/distribution layer and said absorbent core.

2. An absorbent article according to claim 1, wherein each of said at least first and second edge barrier elements comprise at least two parallel stripes.

3. An absorbent article according to claim 1, wherein said at least first and second edge barrier elements are positioned on opposing sides of said longitudinal axis, and each of said first and second edge barrier elements laterally extends partially outside a respective longitudinal edge margin of said absorbent core and/or of said fluid acquisition/distribution layer.

4. An absorbent article according to claim 3, wherein each of said first and second edge barrier element laterally extends along its entire length partially outside the respective longitudinal edge margin of said absorbent core, or of said liquid acquisition/distribution layer.

5. An absorbent article according to claim 1, wherein said at least first and second edge barrier elements are positioned on opposing sides of said longitudinal axis, and each of said first and second edge barrier elements laterally extends partially outside a respective longitudinal edge margin of said absorbent core, wherein said fluid acquisition/distribution layer is wider than said absorbent core.

6. An absorbent article according to claim 1, wherein said at least first and second edge barrier elements are positioned on opposing sides of said longitudinal axis, and each of said first and second edge barrier element laterally extends partially outside a respective longitudinal edge margin of said fluid acquisition/distribution layer, wherein said absorbent core is wider than said fluid acquisition/distribution layer.

7. An absorbent article according to claim 1, wherein said at least first and second edge barrier elements overall cover an area not more than about 60 cm$^2$.

* * * * *